United States Patent [19]
Moulton

[11] Patent Number: 5,277,190
[45] Date of Patent: Jan. 11, 1994

[54] CYCLE LENGTH VARIABILITY IN NONSUSTAINED VENTRICULAR TACHYCARDIA

[75] Inventor: Kreigh P. Moulton, Springfield, Ill.

[73] Assignee: The Board of Regents of the University of Oklahoma, Norman, Okla.

[21] Appl. No.: 864,978

[22] Filed: Apr. 7, 1992

[51] Int. Cl.[5] ........................................ A61B 5/0452
[52] U.S. Cl. .................................... 128/705; 128/703
[58] Field of Search ............... 128/702, 703, 705, 706, 128/708

[56] References Cited

U.S. PATENT DOCUMENTS 5,113,869  5/1992  Nappholz et al. ................... 128/705
5,181,519  1/1993  Bible .................................... 128/702

OTHER PUBLICATIONS

K. P. Moulton et al., "Cylcle Length Variability in Nonsustained Ventricular Tachycardia: A Marker for Inducible Sustained Ventricular Tachycardia", Pace, 13:508 (Apr. 1990).

Primary Examiner—William E. Kamm
Assistant Examiner—Scott M. Getzow
Attorney, Agent, or Firm—Dunlap Codding & Lee

[57] ABSTRACT

The invention disclosed herein describes a method for determining the suitability of a person for extended electrophysiologic testing for ventricular tachycardia comprising monitoring the heart of a person to detect an episode of nonsustained ventricular tachycardia, determining a cycle length variability (CLV) value, and comparing the CLV value to a predetermined threshold number, and making a positive suitability determination if the CLV value is at or below the predetermined threshold number.

5 Claims, 2 Drawing Sheets

CYCLE LENGTH VARIABILITY IN NONSUSTAINED VENTRICULAR TACHYCARDIA

BACKGROUND OF THE INVENTION

1. Field of the Invention

The invention pertains to methods for using information obtained about the physiology of a person to make decisions regarding possible treatment of potentially life-threatening heart disorders, more particularly those disorders of the ventricular arrhythmatic type known to be associated with lethal sustained ventricular tachycardia.

2. Brief Description of the Prior Art

Cardiac arrhythmias are potentially life-threatening irregular heart rhythms usually occurring in the context of a diseased or damaged heart. The most serious cardiac arrhythmias are those originating within the large, lower heart chambers known as the ventricles. In a large proportion of patients who have ventricular arrhythmias, the risk of future sudden death is evaluated by performing a procedure known as an electrophysiologic study (EPS) in which the physician attempts to electrically "induce" an underlying rhythm disturbance known as sustained ventricular tachycardia (SVT). Ventricular tachycardia (VT) is a condition in which the ventricles, or lower chambers, of the heart experience a series of rapid abnormal contractions. If VT can be induced, the patient undergoes appropriate treatment to reduce his future risk of death. If no arrhythmia can be induced, such a risk is acceptably low and no further therapy is recommended.

One ventricular arrhythmia which is commonly seen is known as nonsustained ventricular tachycardia (i.e., ventricular tachycardia which lasts for only short periods) or NSVT. Since a significant number of patients who have NSVT go on to develop the more serious SVT, electrophysiologic testing is usually recommended for them. However, not all persons who have NSVT are subject to inducible arrhythmias and thus derive no benefit by undergoing the electrophysiologic testing.

Because electrophysiologic testing is potentially dangerous and requires expensive hospitalization for periods up to 3-4 weeks, it would be extremely useful to have a physiologic indicator which would help the physician determine which persons would benefit most from EP testing and would decrease the number of patients unnecessarily subjected to EP testing. Such an indicator would also give both the physician and patient the confidence that additional testing is appropriate when indicated.

In some patients with NSVT, a beat-to-beat variation in cycle length (where cycle length is defined as the time interval, measured in milliseconds (msec), between the R wave peaks of successive QRS wave complexes) can be observed to occur. In others, successive cycle lengths appear quite uniform. The degree of variation of cycle lengths during an episode of NSVT is referred to as cycle length variability. Examples of two electrocardiograms which exhibit variability in cycle length are shown in FIG. 1A and FIG. 1B.

Previous work by the inventor revealed that cycle length variability in episodes of NSVT is significantly lower in persons with inducible VT than in persons who experience NSVT but in whom VT is not inducible. K. P. Moulton, et al., "Cycle Length Variability in Nonsustained Ventricular Tachycardia: A Marker for Inducible Sustained Ventricular Tachycardia," PACE, 13:508 (1990). However, this work did not reveal a specific way that a cycle length variability value (hereinafter referred to as CLV) could be used to clearly delineate whether an individual exhibiting episodes of NSVT would be likely to be "inducible" and thus gain benefit from the extensive process of electrophysiologic testing.

BRIEF DESCRIPTION OF THE INVENTION

Figure 2:
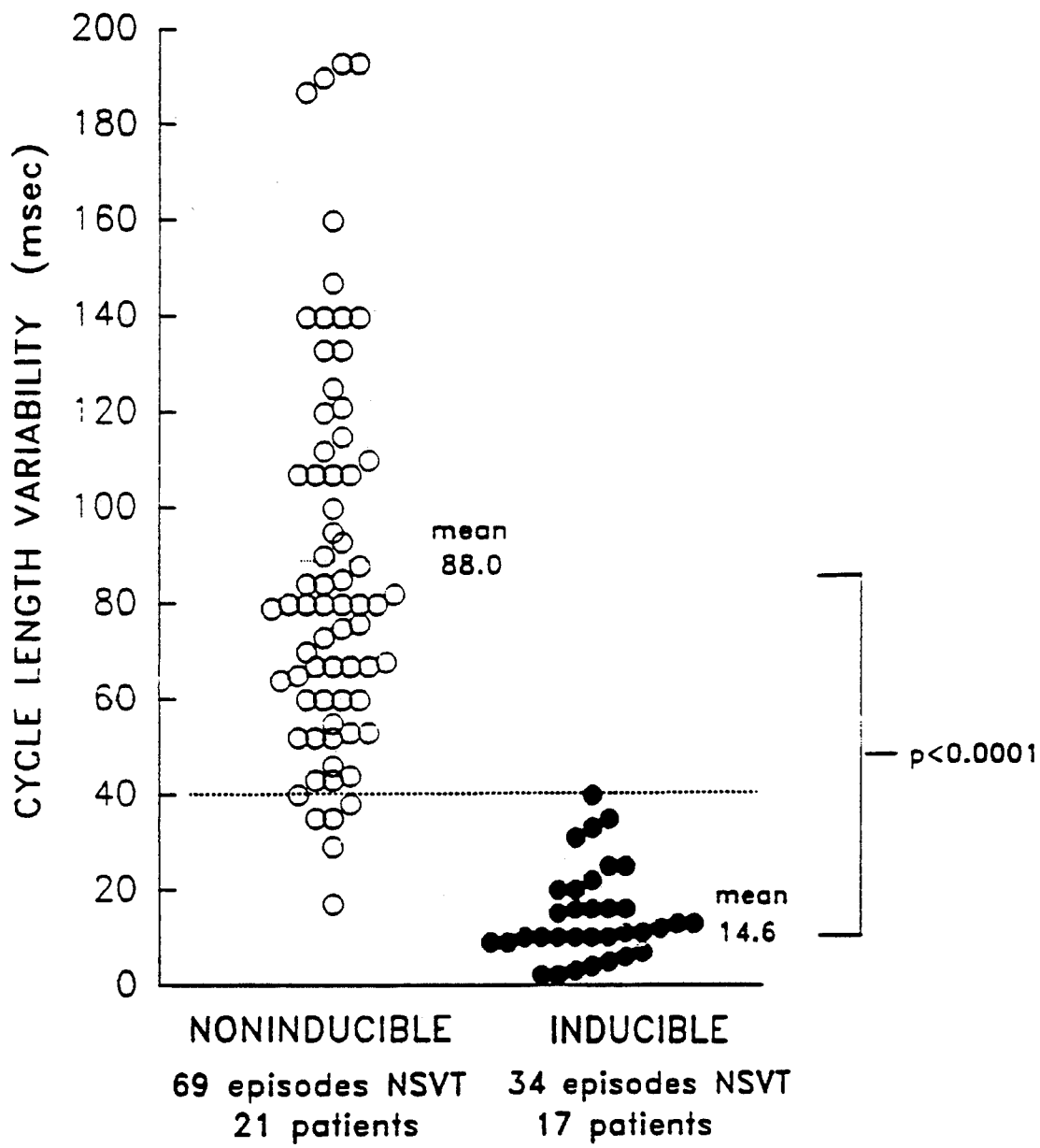
FIG. 2 compares the cycle length variability in episodes of NSVT in persons in which SVT could be induced ("Inducible") versus those in which SVT could not be induced ("Noninducible").

The present invention comprises a method for calculating a CLV in episodes of NSVT and using the CLV for the purpose of determining one's likelihood of being susceptible to the induction of a SVT event during electrophysiological testing by comparing the patient-CLV to an electrophysiologic testing threshold number. Research on 38 persons (see FIG. 2) indicated that all 17 persons tested in whom SVT events were induced during electrophysiologic testing had CLVs values which were at or below 40 milliseconds. On the other hand, of the 69 episodes of NSVT which occurred in the 21 persons in which SVT events were not inducible during electrophysiologic testing, 63 (91%) episodes had CLVs above 40 milliseconds. These results thus reveal a threshold CLV level which can be used in a method to assess the likelihood of successful (i.e., inducible) electrophysiologic testing in persons demonstrating episodes of NSVT. This method will markedly improve the decision-making strategy used by the physician to treat patients with this type of arrhythmia. It will reduce the number of persons subjected to this potentially dangerous procedure and will reduce the number and frequency of unsuccessful electrophysiologic studies thereby improving the benefit to cost ratio of the procedure.

DESCRIPTION OF THE PREFERRED EMBODIMENT

The present invention describes a method for evaluating the potential that a person exhibiting episodes of NSVT is likely to be subject to the inducing of SVT and thus would benefit from a program of electrophysiologic testing to aid in treatment that would reduce the probability that the person would eventually incur a life-threatening or lethal episode of SVT.

In the method described herein, a person who is suspected of having or known to have cardiac arrhythmias is equipped with a heart monitoring device which monitors the heart for an extended period of time. By heart or heart beat monitoring is meant the recording, in the form of an electrocardiogram, of the electrical activity generated by the heart. The monitoring device, which may either be an ambulatory, "holter-type" monitor, or a stationary, non-ambulatory monitor, records the heart beat data of the individual for later examination. The extended period of time of monitoring may last, for example, from 24 to 48 hours for an ambulatory monitor to up to 3 to 4 weeks for non-ambulatory devices used with in-patients. Such ambulatory and non-ambulatory monitors are commercially available and are well known in the art. During the examination of the heart beat data, any episodes of NSVT are identified and characterized. The examination may be visual or it may be done automatically by computer software.

Figure 1:
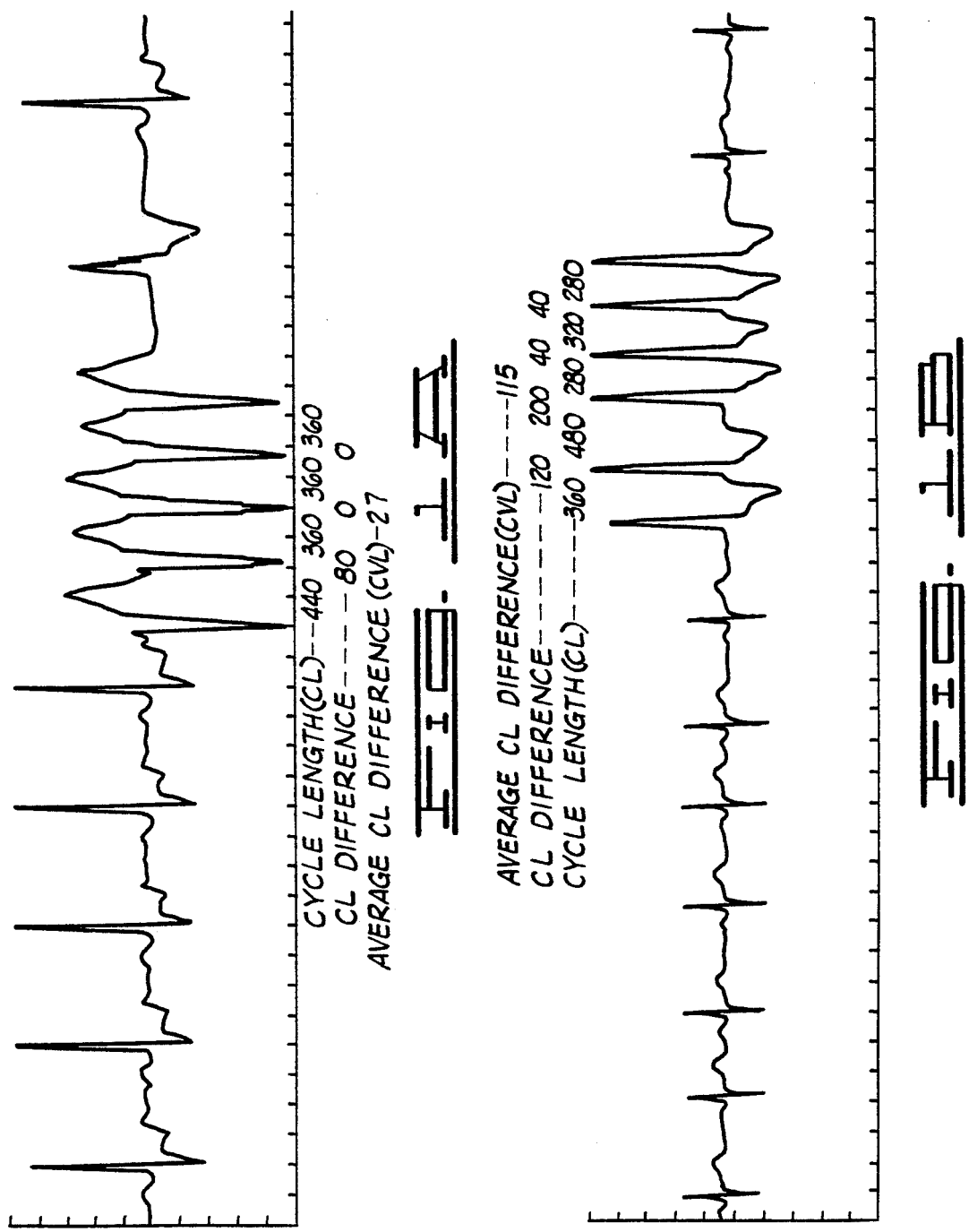
FIG. 1A shows an electrocardiogram exhibiting an episode of nonsustained ventricular tachycardia with a low CLV.
FIG. 1B shows an electrocardiogram exhibiting an episode of nonsustained ventricular tachycardia which a high CLV.

An episode of NSVT is characterized by a sequence of heart beats during which the cycle length is irregular (see FIGS. 1A and 1B). An example of the data which may be recorded from such an episode of irregular cycle lengths is shown in Table I. This data is taken from the electrocardiogram shown in FIG. 1B.

TABLE I

Cycle Length in an Episode of Nonsustained Ventricular Tachycardia and Differences Between Consecutive Cycles

| Cycle | Cycle Length (msec) | Difference (msec) |
|---|---|---|
| 1 | 360 | |
| | | 120 |
| 2 | 480 | |
| | | 200 |
| 3 | 280 | |
| | | 40 |
| 4 | 320 | |
| | | 40 |
| 5 | 280 | |

Average Difference Between Consecutive Cycle Lengths (CLV) = 115 msec

Cycle length is calculated first by measuring the time interval between the R waves of two successive QRS wave complexes. In Table I, the lengths of the five cycles in the episode vary from 280 msec to 480 msec. After the cycle lengths have been calculated, the differences between successive cycle lengths are determined. In Table I, the difference between the first pair of cycle lengths, 360 msec and 480 msec, is 120 msec. The difference between the second pair of cycle lengths, 480 msec and 280 msec, is 200 msec. The difference between the last pair of cycle lengths, 320 msec and 280 msec, is 40 msec. These differences taken from a single episode of NSVT are then averaged to determine the CLV for that episode. In the case of the episode described in Table I, the CLV is 115 msec, and would predict that the person would be noninducible at EP testing, thus sparing the patient of the risks and costs of the EP Study.

The CLV for an episode may be easily calculated by visually assessing a recorded episode outputted on a visual monitor or on a printed medium or it may be calculated automatically by computer software integral to the heart monitoring device itself or to the hardware which analyzes the output of the heart monitoring device. Table I shows an episode lasting for five cycles. A CLV used in the present invention can be calculated from an episode including no less than five cycles.

Once a CLV has been determined for a recorded NSVT episode, the CLV can be compared to a predetermined electrophysiologic testing (EPT) threshold number. An EPT threshold number of 40 msec has been shown to be an exceedingly good indicator of the probability that a person will be "inducible" (if CLV is at or below 40 msec) or will not be "inducible" (if CLV is above 40 msec). However, the EPT threshold number may be selected from a range around 40 msec, for example, from 35 to 45 msec which may be appropriate under certain circumstances.

In the present invention, the authority making a decision regarding admission for in-patient electrophysiologic testing compares the CLV for the patient to the predetermined EPT threshold number. In a case where the threshold number is chosen to be 40 msec, a patient with a CLV of 40 msec or less will be recommended for electrophysiologic testing. If the patient CLV is above 40 msec, the patient will not be recommended for electrophysiologic testing unless there ar other indications that such testing would be useful.

The decision-making authority may be an individual physician, or two or more persons serving in the capacity as a decision-making board. The physician, board or other decision-making authority may base its decision to admit the individual to an in-patient testing facility such as a hospital or medical center in the event that the CLV for the individual under consideration is less than or equal to the predetermined EPT threshold number.

Changes may be made in the embodiments of the invention described herein or in parts of the elements of the embodiments described herein or in the steps or sequence of steps of the methods described herein without departing from the spirit and scope of the invention as defined in the following claims.

What is claimed is:

1. A method for determining the suitability of a person for extended electrophysiologic testing, comprising:

monitoring the heartbeat of the person for an extended period of time with a heart monitoring device;

measuring and recording heart beat cycles in the person during at least one episode of nonsustained ventricular tachycardia;

determining a cycle length variability value for each recorded episode of nonsustained ventricular tachycardia wherein the step of determining a cycle length variability value further comprises:

measuring the length of each cycle which occurs during the recorded episode of nonsustained ventricular tachycardia, calculating the differences in length between consecutive cycles in the episode, and determining the average of the differences for the episode; and comparing at least one determined cycle length variability value to a predetermined electrophysiologic testing threshold number in a range from 35 to 45 milliseconds.

2. The method of claim 1 wherein the step of comparing further comprises a predetermined electrophysiologic testing threshold number of 40 milliseconds.

3. The method of claim 1 wherein the step of determining the average of the differences, further comprises an average based on at least five lengths.

4. A method for evaluating a person for admission to in-patient electrophysiologic testing, comprising:

monitoring a heatbeat of a person with a heart monitoring device for a extended period of time;

measuring and recording heart beat cycles in the person during at least one episode of nonsustained ventricular tachycardia;

determining at least one cycle length variability value by:

measuring the length of each cycle within an episode;

calculating the differences in length between consecutive cycles in the episode, and determining the average of the differences for the episode to obtain a cycle length variability value;

comparing the determined cycle length variability value to a predetermined electrophysiologic testing threshold number in a range from 35 to 45 milliseconds; and admitting the person to an in-patient electrophysiologic testing facility if the determined cycle length variability value is less than or equal to the predetermined electrophysiologic testing threshold number.

5. The method of claim 4 wherein the step of comparing further comprises a predetermined electrophysiologic threshold number of 40 milliseconds.

* * * * *